(12) United States Patent
Akridge et al.

(10) Patent No.: US 7,789,092 B2
(45) Date of Patent: Sep. 7, 2010

(54) METHOD FOR ENHANCING THE SHAVING PROCESS FOR HUMANS USING AN OSCILLATING SKIN BRUSH

(75) Inventors: Robert E. Akridge, Seattle, WA (US); Kenneth A. Pilcher, Seattle, WA (US)

(73) Assignee: Pacific Bioscience Laboratories, Inc., Bellevue, WA (US)

( * ) Notice: Subject to any disclaimer, the term of this patent is extended or adjusted under 35 U.S.C. 154(b) by 894 days.

(21) Appl. No.: 11/316,055

(22) Filed: Dec. 21, 2005

(65) Prior Publication Data

US 2007/0142845 A1 Jun. 21, 2007

(51) Int. Cl.
*A45D 24/00* (2006.01)
(52) U.S. Cl. ..................................... 132/200
(58) Field of Classification Search ................. 132/200, 132/289, 290, 292; 604/289; 606/131; 15/28, 15/22.1, 21.1, 97.1; 601/114, 142
See application file for complete search history.

(56) References Cited

U.S. PATENT DOCUMENTS 3,968,789 A * 7/1976 Simoncini .................. 601/95
4,203,431 A * 5/1980 Abura et al. ................... 601/6
4,998,545 A * 3/1991 Hiromura .................. 132/290
2005/0278877 A1* 12/2005 Akridge et al. ................. 15/28

OTHER PUBLICATIONS

How to get the perfect shave. Corey Greenberg, Weekend Today Jan. 30, 2005.*

* cited by examiner

*Primary Examiner*—Cris L Rodriguez
*Assistant Examiner*—Rachel R Steitz
(74) *Attorney, Agent, or Firm*—Clark A. Puntigam; Jensen & Puntigam, P.S.

(57) ABSTRACT

The method includes the steps of preparing a beard or other skin area to be shaved for shaving by first applying the tips of a bristle skin brush to the skin area of the beard to clean the skin area, the brush having an outer brushhead portion and an inner brushhead portion, wherein the first portion remains stationary in operation, wherein the second brushhead portion oscillates through a selected range 18-26° at a frequency within the range of 120-220 Hz. The tips of the bristles are applied to the skin area to be shaved following or simultaneous with the wetting of the skin area with water, and then following or simultaneous with, lathering the skin area with shaving cream or gel.

5 Claims, 2 Drawing Sheets

METHOD FOR ENHANCING THE SHAVING PROCESS FOR HUMANS USING AN OSCILLATING SKIN BRUSH

TECHNICAL FIELD

This invention relates generally to methods of shaving, and more specifically concerns such methods using a sonic frequency skin brush.

BACKGROUND OF THE INVENTION

Daily facial shaving is typically a somewhat laborious and often unpleasant task, and in addition often produces unsatisfactory results. Historically, a number of factors have been recognized to be important in obtaining a close and comfortable shave. These include adequate cleansing of the face, softening of the beard, lubricating the beard, redirecting the individual hairs of the beard so that they are oriented in a common direction, and directing the razor blade as close to the base of each hair as possible.

While the above steps are all important relative to use of a razor blade in shaving, several of the steps are important with use of an electric razor as well. Typically, however, it is recognized that the closest shave occurs with the use of a razor blade.

Even when careful attention is paid to the above factors, often a close shave is still not obtained. Also, in many cases a shave, whether close or not, may not be very comfortable.

Further, it is generally recognized that razor blade shaving has not seen significant improvements for some time. While some new products have come on the market, including hand-held razors with multiple razor blades, facial shaving is still generally regarded to be an inefficient, irritating process. Preparation of the beard, including adequate wetting of the beard and careful application of shaving cream, does produce improved results. The use of a high quality barber brush is also frequently recommended for improved results. However, the lack of time and the cost of a high quality barber brush, as well as the increase in inexpensive but low quality disposable razors, has generally prevented most men from experiencing a truly close and comfortable shave.

Accordingly, it is desirable to prepare the beard in such a manner that a quality hand-held razor can provide a close and comfortable shave.

SUMMARY OF THE INVENTION

Accordingly, the present invention is a method for improving shaving of hair from skin in humans, comprising the steps of:

preparing a skin area with hair for shaving by applying the tips of a bristled skin brush to the hair area, the brush having an outer brushhead portion and an inner brushhead portion, wherein the first portion remains stationary and wherein the second portion oscillates through a selected angle in the range of 18-26° at a frequency in the range of 120-220 Hz, thereby producing a cleansing effect on the skin by exfoliation of skin cells at the base of the facial hairs and an orienting effect on said hairs so as to improve the shaving process.

BEST MODE FOR CARRYING OUT THE INVENTION

Figure 1:
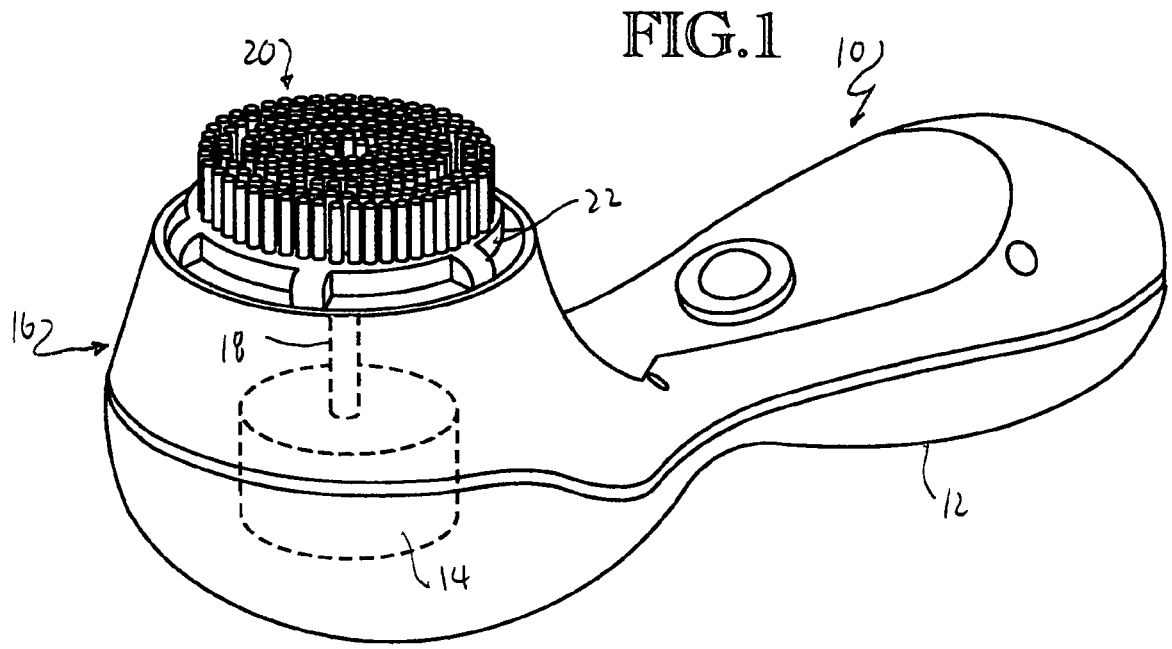
FIG. 1 is a perspective view of a skin care brush used in the method of the present invention.
Figure 2:
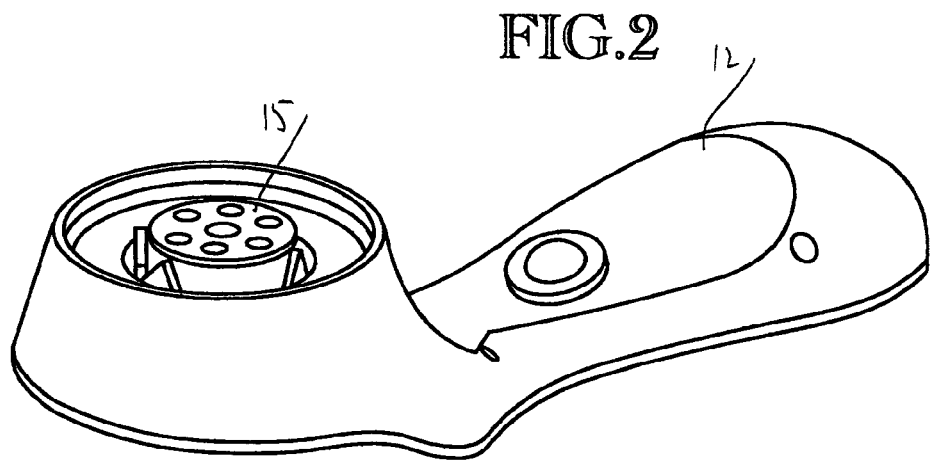
FIG. 2 is a perspective view showing a handle portion of the skin care brush of FIG. 1.
Figure 3:
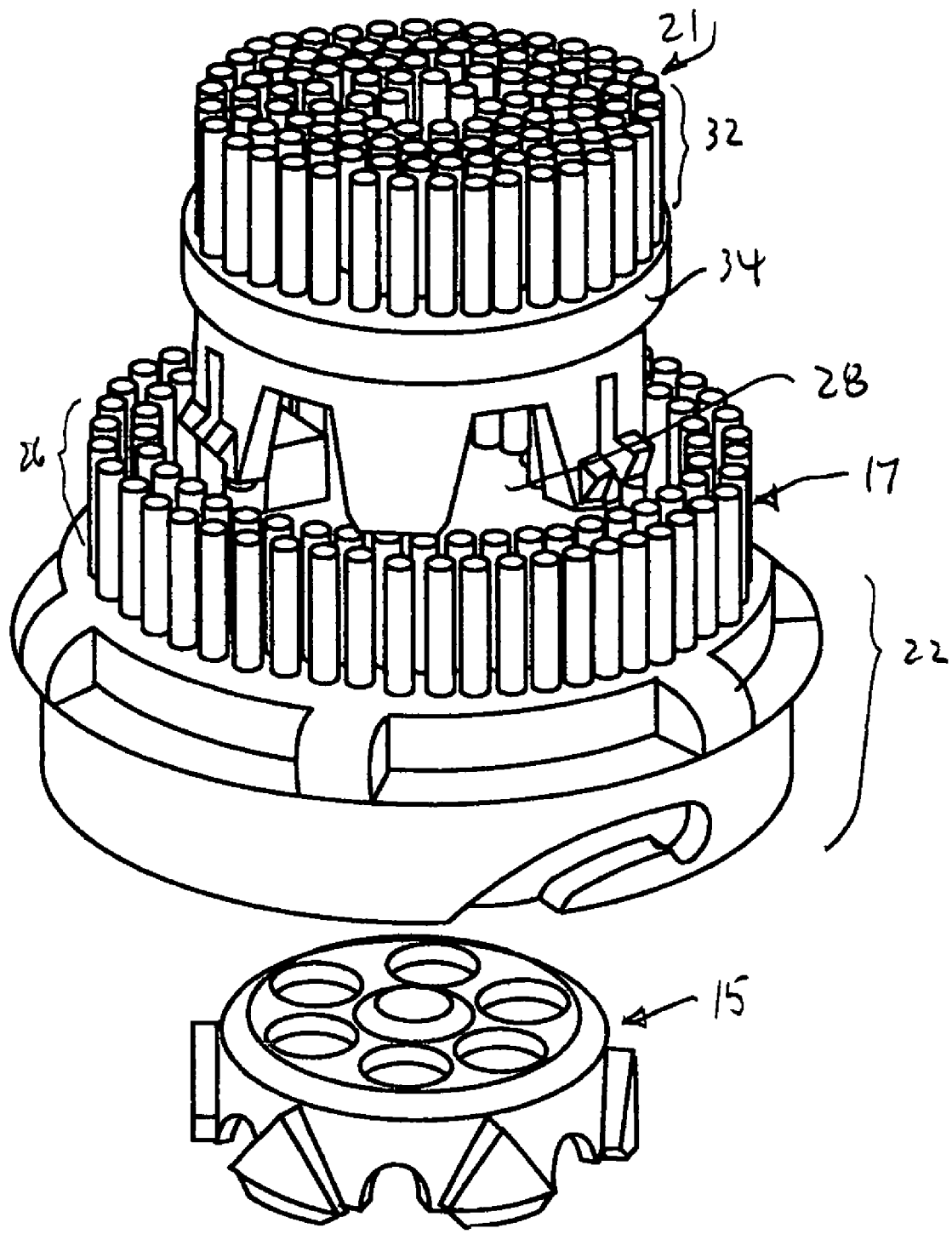
FIG. 3 is an exploded view showing the brush portion of the brush of FIG. 1.

FIGS. 1, 2 and 3 show a skin brush which is used in a shaving method which results in a close and comfortable shave with a hand-held razor. The brush appliance, which is shown at 10 in FIG. 1, is described in more detail in three co-pending applications: U.S. patent application Ser. No. 10/873,352, for OSCILLATING BRUSHHEAD ATTACHMENT SYSTEM FOR A PERSONAL CARE APPLIANCE; U.S. patent application Ser. No. 10/873,564, for MOTOR FOR PROVIDING OSCILLATING ACTION FOR A PERSONAL CARE APPLIANCE; and U.S. patent application Ser. No. 10/873,584, for BRUSH CONFIGURATION FOR A POWERED SKIN CLEANSING BRUSH APPLIANCE, all of which are owned by the assignee of the present invention. The contents of those applications are hereby incorporated by reference.

The personal care appliance 10 includes, in general, a handle 12 with an oscillating motor assembly 14 located in the body 16 of the appliance, the motor assembly driving an armature 18 and a brushhead assembly 20 through an angle within the range of 18-26° at a frequency in the range of 120-220 Hz. The brushhead assembly is mounted to a drive hub 15 which is driven by the armature, and includes an outer brushhead portion 17 and an inner brushhead portion 21. The outer brushhead portion remains stationary during operation of the appliance, while the inner brushhead portion oscillates through the specified angle, which is in the range of 18-26°.

In the particular embodiment shown, the outer brushhead portion 17 includes a base member 22, which is configured to help the user in the installation and removal of the brushhead assembly relative to the drive hub 15. Extending upwardly from base 22 are brushhead bristles 26 which, in the embodiment shown, comprise two concentric, adjacent rings of bristle tufts. The bristles could be nylon or elastomeric. The outer ring of bristles has a diameter of approximately 1.53 inches, while the diameter of the inner ring of bristles is approximately 1.39 inches. The arrangement of the bristles is circular, which is preferred, although not necessary.

The inner brushhead portion 21 has a generally circular configuration and is arranged to fit into a central opening 28 of outer brushhead portion 17. In some arrangements, there could be a gap between the bristles in the inner brushhead portion and the bristles in the outer brushhead portion. Typically, this gap is in the range of 0.050-0.125 inches, preferably 0.084 inches.

The inner brushhead portion includes a plurality of inner brushhead bristle tufts 32 arranged in a circular pattern covering the entire upper surface of a base portion 34 in which they are mounted and extend upwardly therefrom.

The base portion 34 of the inner brushhead portion is arranged to snap into place and to be conveniently removable from driving hub 15. This arrangement is described in substantial detail in the 10/873,352 application. The inner brushhead portion is arranged structurally relative to the outer brushhead portion and the remainder of the device such that it is free to rotate relative to the outer brushhead portion which remains stationary, but is retained within the outer brushhead portion by its connection with the drive hub 15. The arrangement is such that the entire brushhead assembly 20 may be removed as a unit from the drive hub 15. The inner brushhead assembly 21 is also removable from the outer brushhead portion 17.

The optimum ranges for the important bristle characteristics and tuft requirements to provide the best performance and cleansing feel/impression for the present shaving method depends to an extent upon the energy which is generated by the appliance in operation, which depends in turn upon both frequency and amplitude of bristle movement. For a frequency in the range of 120-220 Hz and amplitude in the range of 18-26°, the length of Tynex (DuPont) type bristles will be between 0.3 and 0.425 inches, with a desired diameter of approximately 3 mils. With Super-Soft (DuPont) bristles, the length of the bristles is also between 0.3 and 0.425 inches, while the diameter of the bristles can vary between 3 and 4 mils.

The bristles and their arrangement are also important relative to effective drying of the brush after it has been used. The general range for the number of tufts is 40-100 in the outer brushhead portion 17, and 40-120 in the inner brushhead portion 21. The preferred bristle tuft range is 60-90 for the outer brushhead portion and 70-110 for the inner brushhead portion, with 80 and 90 being optimal, respectively. The tufts should be evenly spaced.

The above-described brush is used in the shaving preparation method disclosed herein. The skin brush 10 is first turned on and the tips of the bristles are applied against the facial area of the user, which typically has been wetted. The action of the bristles, with the above amplitude and frequency, initially produces an exfoliating effect, removing dead skin cells from the base of the hairs of the beard. This effect allows the hairs to sit more erect from the skin. At the same time, as the skin brush is passed back and forth over the user's facial skin, the hairs are generally forced to point in the same direction. This has advantages for achieving a clean shave.

Water is then added to the beard by the user. When the facial area is thus wetted, the brush is then again applied against the facial area. The action of the brush with the water generates fluid forces as the brush is moved back and forth across the face. The bristles of the brush push the hairs back and forth, while at the same time moving the water past the hairs, such that the individual hairs absorb the water to a significant extent, significantly greater than by just manual application. The increased water absorption of the individual hairs has a significant effect on shaving, in that it plumps the individual hairs, makes them erect and primed for use of a manual razor blade.

Shaving cream or gel is then applied by the user to the facial area, using the skin brush. The application of the shaving cream with the skin brush enables the shaving cream to come in closer contact with the individual hairs of the beard, enabling the hairs to be cut closer and with less friction by a razor than if the cream/gel had been applied just by hand.

Thus, using the skin brush as described above, in the specified frequency and amplitude ranges, in the steps outlined above, in combination with the application of water and a shaving cream or gel, results in a cleaner, closer and more comfortable shave.

While shaving with a razor has been described in the context of facial shaving, it should be understood that shaving of other parts of the body, such as legs for instance, can be readily accomplished as well. Further, shaving with an electric razor can also be accomplished by using the present method, although there will be no application of shaving cream. Any preparation of the skin area prior to shaving otherwise used for shaving with an electric razor can be used as part of the method disclosed above.

Although a preferred embodiment has been disclosed herein for purposes of illustration, it should be understood that various changes, modifications, and substitutions may be incorporated in the method without departing from the spirit of the invention, which is defined by the claims which follow.

What is claimed is:

1. A method for improving shaving of hair from skin in humans, comprising the steps of:
   preparing a skin area with hair for shaving by applying tips of a bristled power skin brush to the skin area, wherein the skin area includes a facial surface and the hairs form a facial beard or wherein the skin area includes a non-facial skin area, including legs of a human, the power skin brush having an outer brushhead portion and an inner brushhead portion, wherein the first portion remains stationary and wherein the second portion oscillates through a selected angle in the range of 18-26° at a frequency in the range of 120-220 Hz, thereby producing a cleansing effect on the skin by exfoliation of skin cells at the base of the facial hairs and an orienting effect on said hairs so as to improve the shaving process; and
   adding water to the skin area, in the absence of shaving cream, following the step of preparing, and thereafter applying the moving bristle tips of the power skin brush to the wetted skin area, wherein the movement of the bristles through said angle and at said frequency over the wetted skin area is such that it aids in the absorption of water by the hairs on the skin area, improving shaving.

2. The method of claim 1, including the further step of applying shaving cream or gel to the skin area in such a manner as to facilitate shaving with the moving bristle tips, thereby improving shaving.

3. The method of claim 2, wherein shaving is carried out with a razor.

4. The method of claim 2, wherein shaving is carried out with an electric razor.

5. The method of claim 1, including the step of wetting the skin area prior to the initial application of the tips of the bristled skin brush to the skin area.

* * * * *